(12) United States Patent
Jung et al.

(10) Patent No.: US 8,241,831 B2
(45) Date of Patent: Aug. 14, 2012

(54) ACID GENERATING AGENT FOR CHEMICALLY AMPLIFIED RESIST COMPOSITIONS

(75) Inventors: Sung-Do Jung, Chungcheongnam-do (KR); Jin-Ho Kim, Daejeon-gwangyeoksi (KR); Jung-Hoon Oh, Chungcheongnam-do (KR); Hyun-Soon Lim, Chungcheongnam-do (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 789 days.

(21) Appl. No.: 12/231,814

(22) Filed: Sep. 5, 2008

(65) Prior Publication Data

US 2009/0291390 A1 Nov. 26, 2009

(30) Foreign Application Priority Data

May 21, 2008 (KR) .................. 10-2008-0046898

(51) Int. Cl.
G03F 7/004 (2006.01)
C07C 309/65 (2006.01)
(52) U.S. Cl. .............. 430/270.1; 430/910; 430/921; 562/101; 562/113; 568/28
(58) Field of Classification Search .......... 430/270.1, 430/910, 921; 562/101, 109, 113; 568/28
See application file for complete search history.

(56) References Cited

U.S. PATENT DOCUMENTS 7,511,169 B2 * 3/2009 Ohsawa et al. ............ 562/30
7,514,202 B2 * 4/2009 Ohsawa et al. ............ 430/270.1
7,531,290 B2 * 5/2009 Kobayashi et al. ........ 430/270.1
2006/0228648 A1 * 10/2006 Ohsawa et al. ............ 430/270.1
2007/0099112 A1 * 5/2007 Kobayashi et al. ........ 430/270.1

FOREIGN PATENT DOCUMENTS

JP 10-2007-0046744 5/2007

* cited by examiner

Primary Examiner — John Chu
(74) Attorney, Agent, or Firm — Davidson, Davidson & Kappel, LLC

(57) ABSTRACT

An acid generating agent represented by the following formula (1) or (2) is provided, which is included in chemically amplified resist compositions:

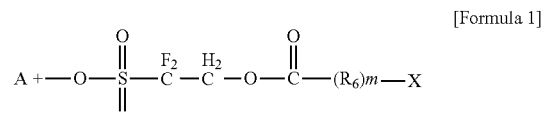

[Formula 1]

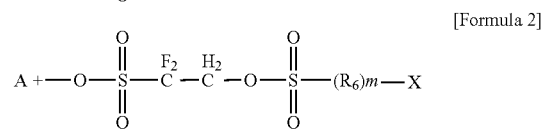

[Formula 2]

wherein in the formula (1) and (2), X represents an unsubstituted or substituted alkyl group having 1 to 20 carbon atoms and selected from alkyl, haloalkyl and alkylsulfonyl, which may have at least one hydrogen atom substituted by an ether group, an ester group, a carbonyl group, an acetal group, a nitrile group, a cyano group, a hydroxyl group, a carboxyl group or an aldehyde group, or represents a perfluoroalkyl group having 1 to 4 carbon atoms; $R_6$ represents an alkyl group having 1 to 10 carbon atoms, an alkoxy group having 1 to 10 carbon atoms, or a heteroatom selected from nitrogen, sulfur, fluorine and oxygen; m is an integer from 0 to 2; and A+ is an organic counterion.

9 Claims, 9 Drawing Sheets

[Synthesis Example 1]-1

[Synthesis Example 1]-2

[Synthesis Example 2]-1

[Synthesis Example 2]-2

FIG.6
[Synthesis Example 3]-1
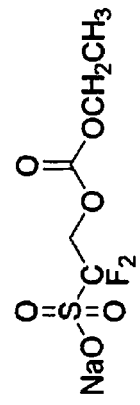
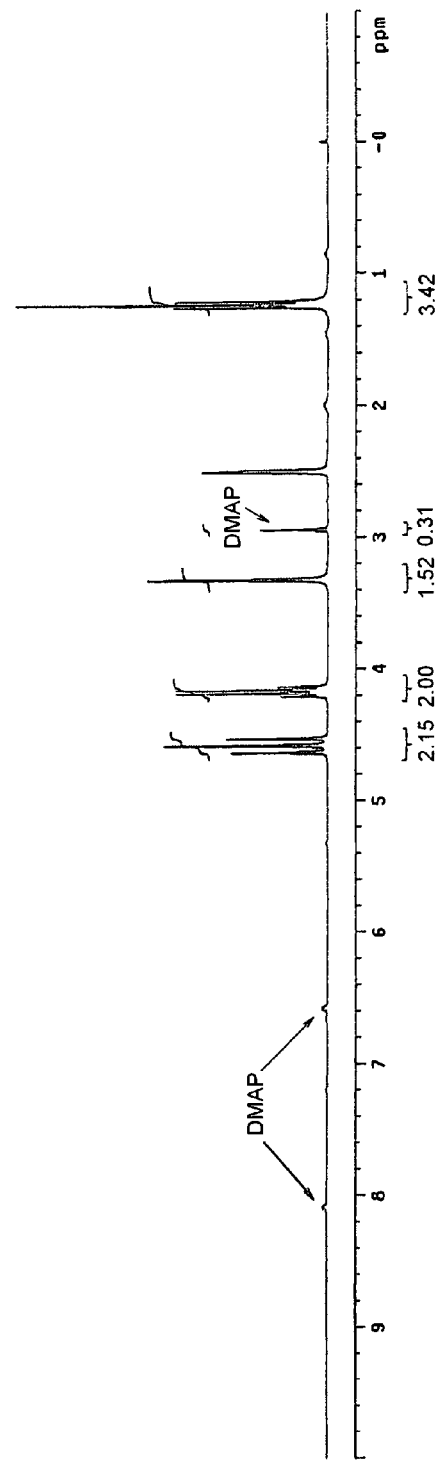

[Synthesis Example 3]-2

[Synthesis Example 4]-2

ACID GENERATING AGENT FOR CHEMICALLY AMPLIFIED RESIST COMPOSITIONS

This application claims priority under 35 U.S.C §119 from Korean Patent Application 10-2008-0046898, filed on May 21, 2008, the contents of which are hereby incorporated by reference in their entirety for all purposes as if fully set forth herein.

BACKGROUND OF THE INVENTION

1. Field of the Invention

The present invention relates to an acid generating agent, and more particularly, to a salt suitable as an acid generating agent used in chemically amplified resist compositions that are used in semiconductor processes.

2. Description of the Related Art

A chemically amplified resist composition used in the semiconductor fine processing utilizing lithography contains an acid generating agent, and as the technologies supporting the semiconductor fine processing continue to develop, a demand for resists with higher resolution still exists.

Therefore, in order to produce a resist having an increased resolution and desired properties, a large number of different acid generating agents have been developed.

Development of photo-acid generating agents for chemically amplified resists has been carried out such that low sensitivity ionic photo-acid generating agents such as iodonium salts were initially used, and at the same time, non-ionic photo-acid generating agents were developed, so that such an agent would generate a sulfonic acid derivative such as toluenesulfonic acid, when irradiated with light, and induce a deprotection reaction for resins. Thereafter, the tendency has been such that more derivatives of sulfonyl salts having faster response time are produced, and modification is more weighted on the cation part, thus resulting in a variety of sulfonyl salts.

According to the recent trend in the development of finely patterned resists requesting even smaller line widths, the line edge roughness of resist has been the most urgent problem to be addressed. Furthermore, there is rising another problem of reducing the amount of the salt of a photo-acid generating agent eluted into water, as water is used in the processes of argon fluoride (ArF) immersion lithography. In an attempt to improve the circumstances, the development of photo-acid generating agents began to involve modification of the anion part, in view of improving the diffusion rate of acid and transparency, and reducing the elution of the photo-acid generating agent into water. Furthermore, new inventions focused on the anion moiety of acid generating agents have recently been achieved, on the bases of numerous experimental results and reports showing that the anion moiety has substantially greater influence than the cation moiety on the physical and chemical characteristics which can improve the fluidity of acid and the properties of the resist composition. Thus, the trend of the development is now focused on photo-acid generating agents that are capable of reducing the diffusion rate of acid, and have good transmissibility of ArF laser at 193 nm.

Therefore, attempts are rapidly being made to introduce a bulky alicyclic ring, or an alkyl group, alkoxy group or ether group having a large number of carbon atoms into a salt suitable as a photo-acid generating agent (see Korean Patent Application No. 10-2006-0114104, 10-2007-0069049, 10-2005-0107599 and 10-2007-0053619).

SUMMARY OF THE INVENTION

In order to overcome such problems as described above, there is provided, according to an aspect of the present invention, a novel acid generating agent useful for chemically amplified resist compositions, which agent has excellent resolution and line width roughness, and is eluted less readily into water in the processes of ArF immersion lithography.

According to another aspect of the present invention, there is provided an intermediate used in the production of the acid generating agent, and a method for synthesizing the intermediate substance.

However, the technical problems addressed by the present invention are not limited only to the problems mentioned in the above, and other technical problems will be clearly understood by a person ordinarily skilled in the art from the following descriptions.

According to an embodiment of the present invention, there is provided an acid generating agent represented by the following formula (1):

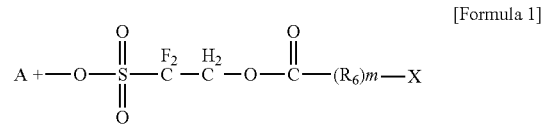

[Formula 1]

wherein X represents an unsubstituted or substituted alkyl group having 1 to 20 carbon atoms and selected from alkyl, haloalkyl and alkylsulfonyl, which may have at least one hydrogen atom substituted by an ether group, an ester group, a carbonyl group, an acetal group, a nitrile group, a cyano group, a hydroxyl group, a carboxyl group or an aldehyde group, or represents a perfluoroalkyl group having 1 to 4 carbon atoms; $R_6$ represents an alkyl group having 1 to 10 carbon atoms, an alkoxy group having 1 to 10 carbon atoms, or a heteroatom selected from nitrogen (N), sulfur (S), fluorine (F) and oxygen (O); m is an integer from 0 to 2; and A+ is an organic counterion.

According to another embodiment of the present invention, there is provided an acid generating agent represented by the following formula (2):

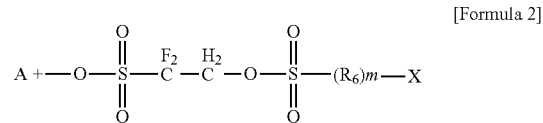

[Formula 2]

wherein X represents an unsubstituted or substituted alkyl group having 1 to 20 carbon atoms and selected from alkyl, haloalkyl and alkylsulfonyl, which may have at least one hydrogen atom substituted by an ether group, an ester group, a carbonyl group, an acetal group, a nitrile group, a cyano group, a hydroxyl group, a carboxyl group or an aldehyde group, or represents a perfluoroalkyl group having 1 to 4 carbon atoms; $R_6$ represents an alkyl group having 1 to 10 carbon atoms, an alkoxy group having 1 to 10 carbon atoms, or a heteroatom selected from N, S, F and O; m is an integer from 0 to 2; and A+ is an organic counterion.

According to another embodiment of the present invention, there are provided an intermediate used in the production of an acid generating agent, and a method for synthesizing the intermediate.

According to another embodiment of the present invention, there is provided a chemically amplified resist composition containing the acid generating agent.

Further specific matters of the embodiments of the present invention will be revealed by the following detailed description.

The acid generating agent according to embodiments of the present invention has intermediate physical properties in terms of diffusion rate or dispersibility, when compared to those photo-acid generating agents based on an anion having a bulky alicyclic ring, and those photo-acid generating agents having relative short chains and having hydrophobic characteristics, such as the existing trifluoromethanesulfonate or nonafluorobutanesulfonate type agents, and thus is advantageous in controlling the diffusion rate and the degree of dispersion upon realizing resists with high resolution.

BRIEF DESCRIPTION OF THE DRAWINGS

FIG. 6 is a $^1$H-NMR spectrum of the compound produced according to Synthesis Example 3-1;

DESCRIPTION OF THE PREFERRED EMBODIMENTS

Figure 1:
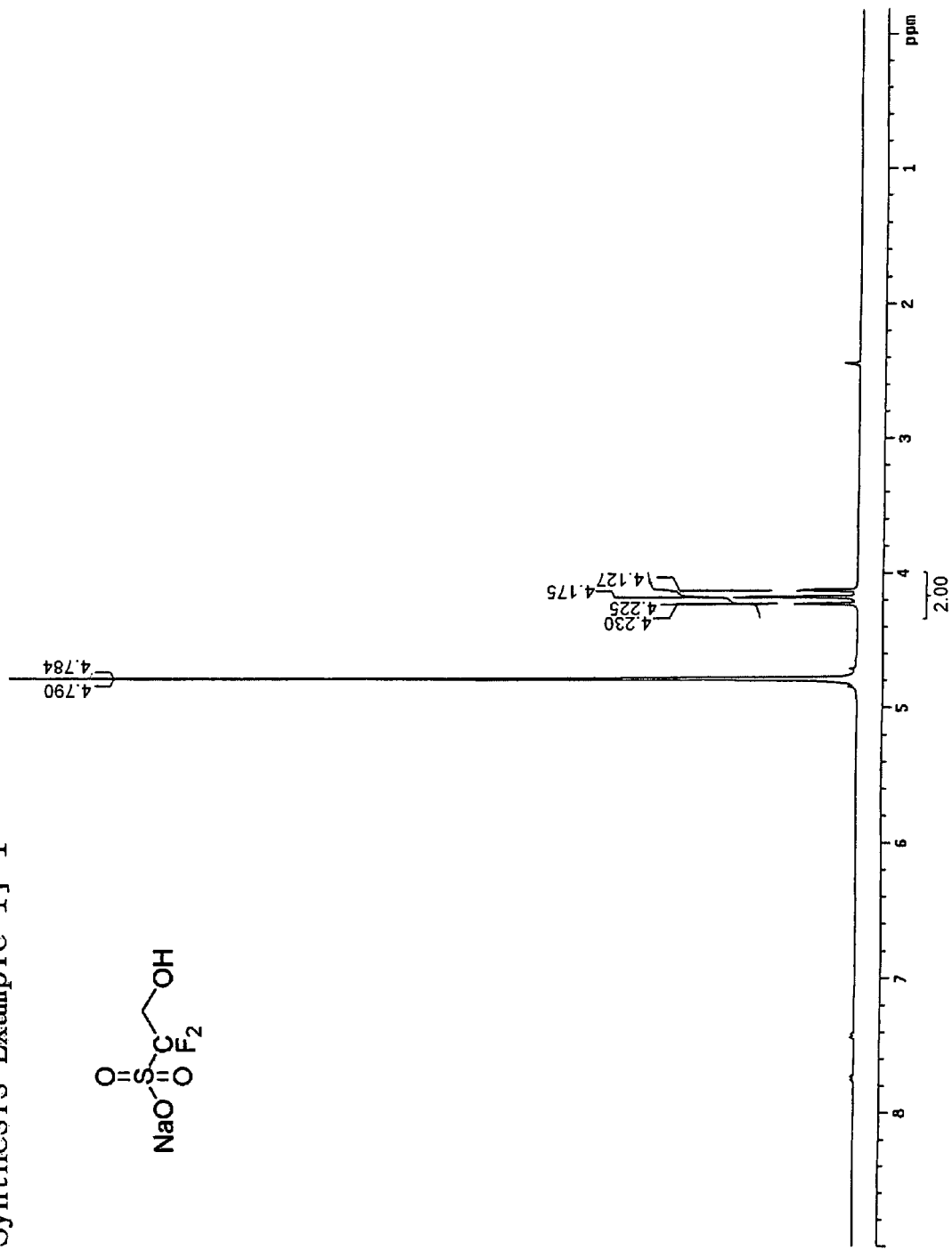
FIG. 1 is a $^1$H-NMR spectrum of the compound produced according to Synthesis Example 1-1.
Figure 2:
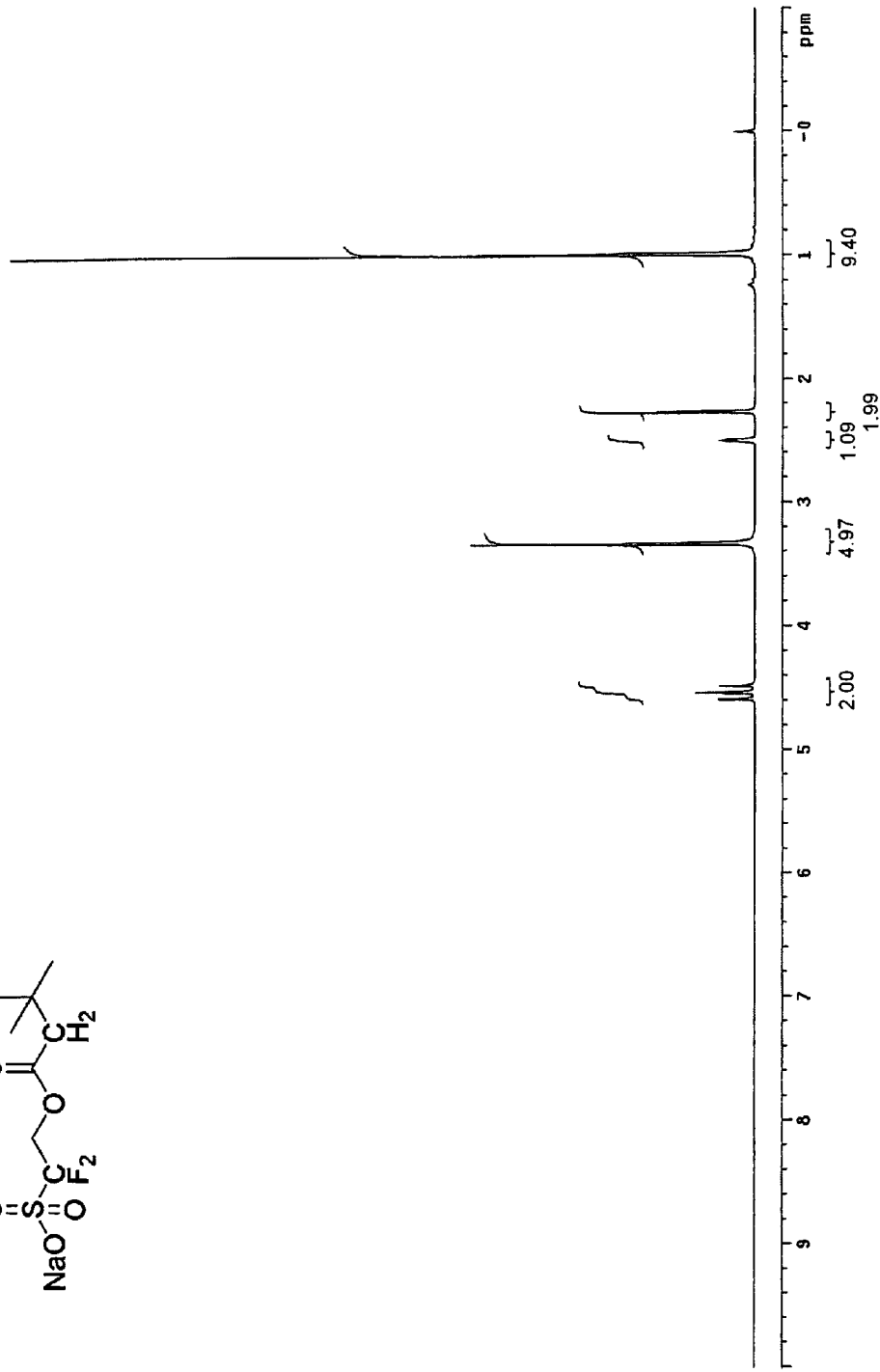
FIG. 2 is a $^1$H-NMR spectrum of the compound produced according to Synthesis Example 1-2.
Figure 3:
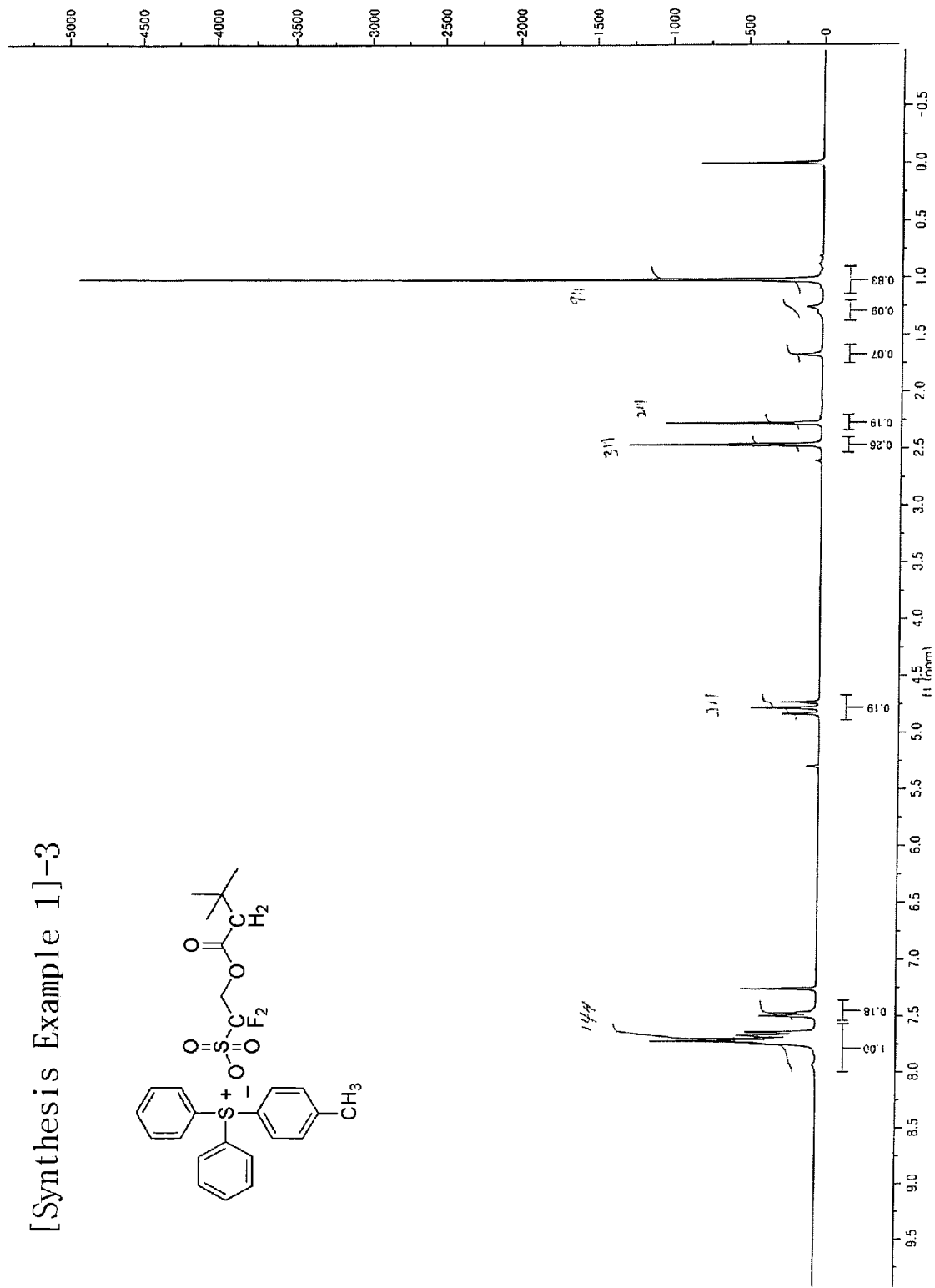
FIG. 3 is a $^1$H-NMR spectrum of the compound produced according to Synthesis Example 1-3.
Figure 4:
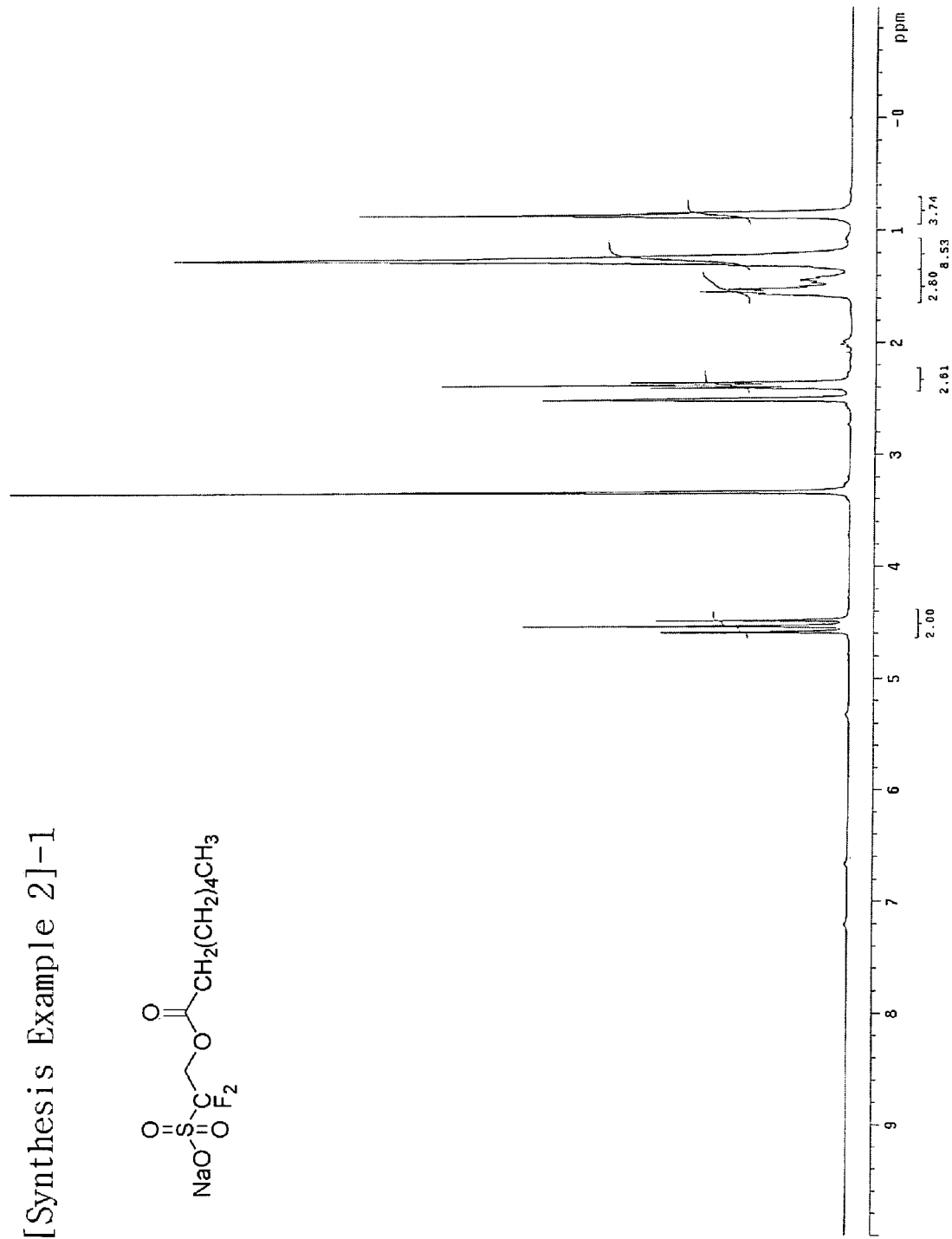
FIG. 4 is a $^1$H-NMR spectrum of the compound produced according to Synthesis Example 2-1.
Figure 5:
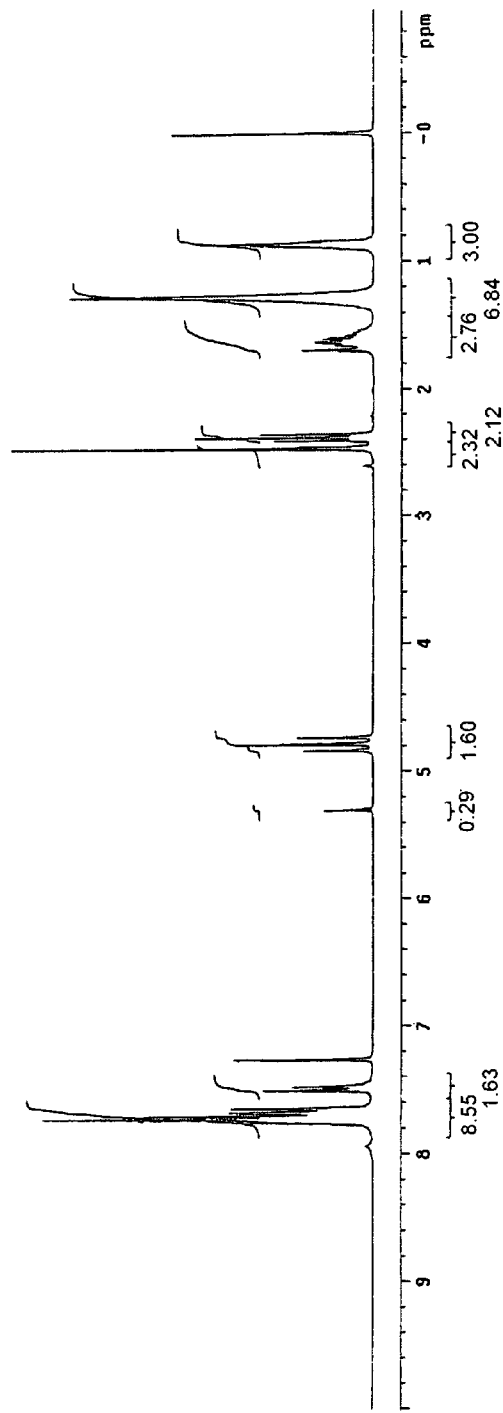
FIG. 5 is a $^1$H-NMR spectrum of the compound produced according to Synthesis Example 2-2.
Figure 7:
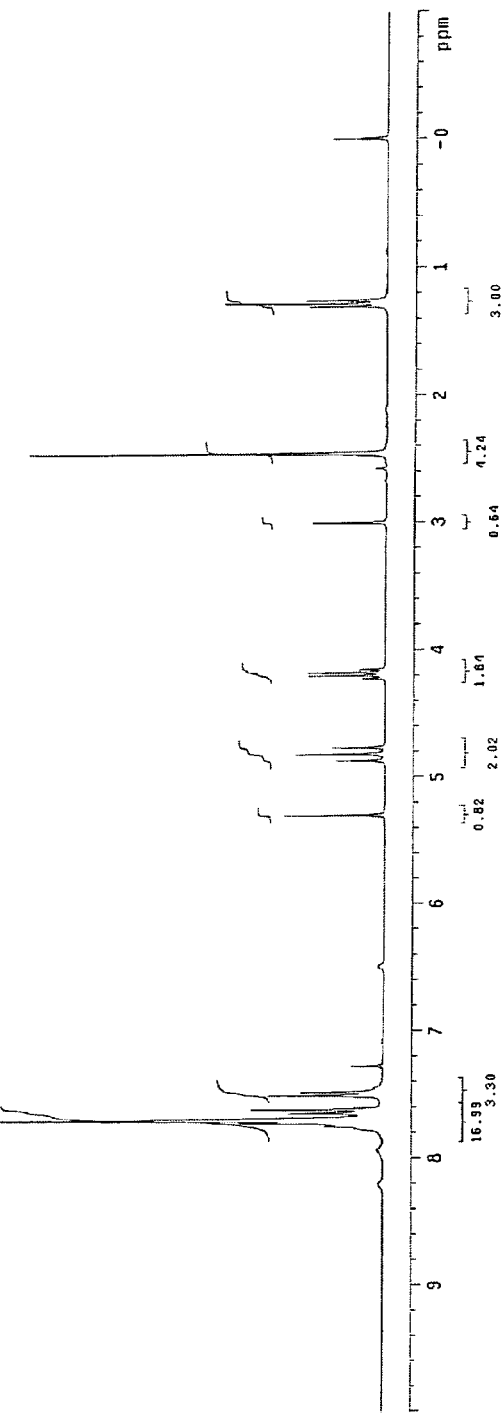
FIG. 7 is a $^1$H-NMR spectrum of the compound produced according to Synthesis Example 3-2.
Figure 8:
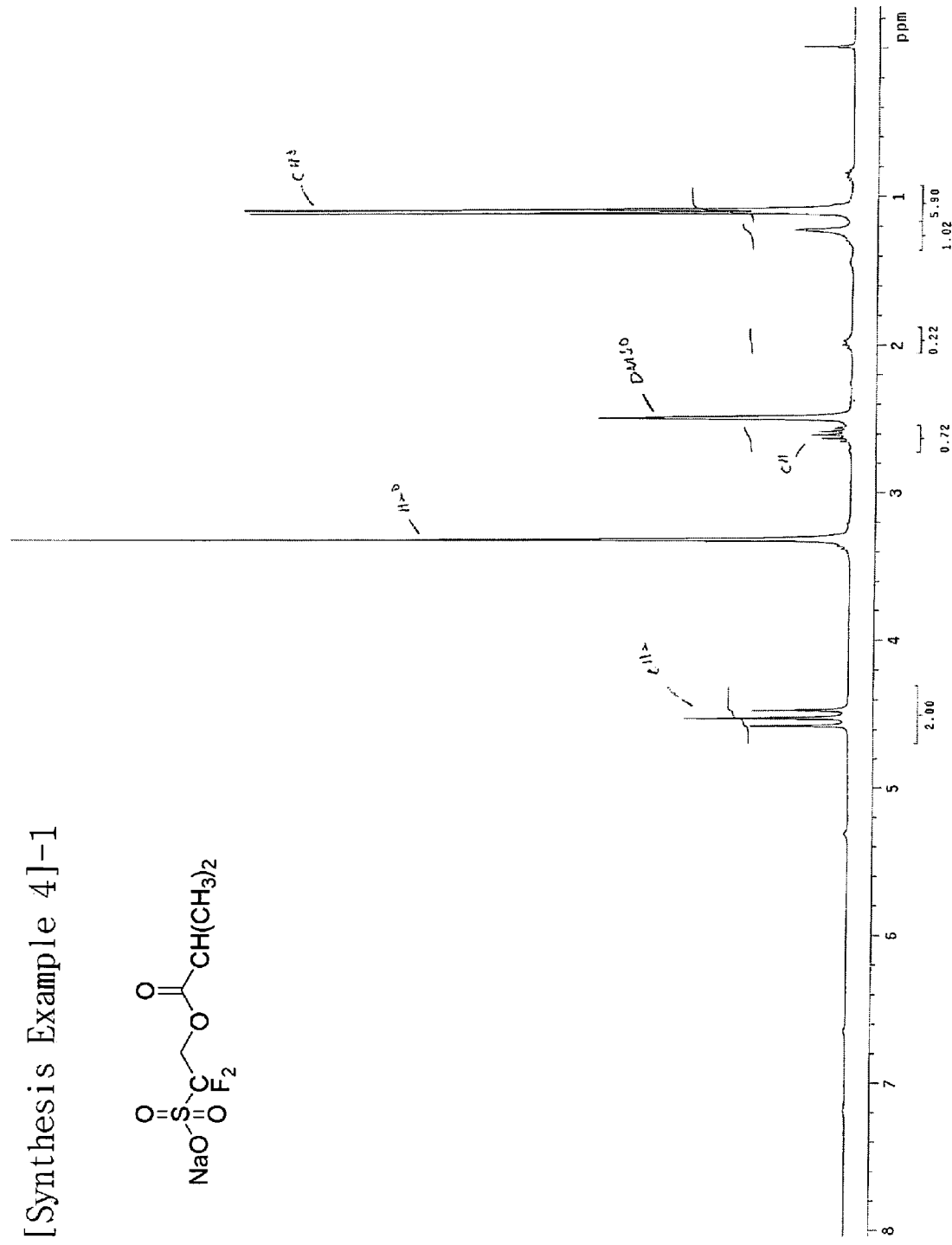
FIG. 8 is a $^1$H-NMR spectrum of the compound produced according to Synthesis Example 4-1.
Figure 9:
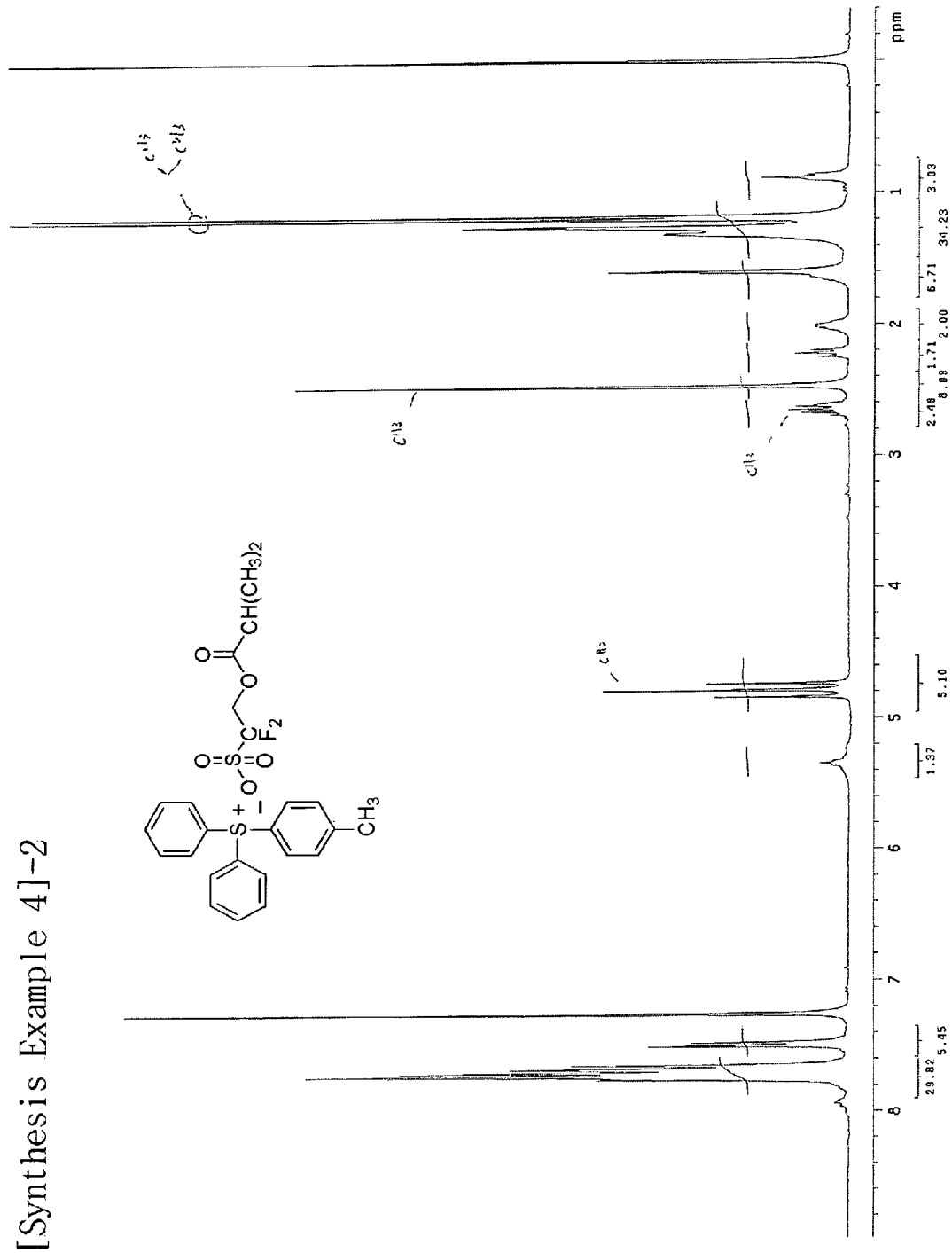
FIG. 9 is a $^1$H-NMR spectrum of the compound produced according to Synthesis Example 4-2.

Hereinafter, the embodiments of the present invention will be described in detail. However, these embodiments are suggested only for illustrative purposes, and do not intend to limit the present invention by any means. The present invention is defined only by the scope of the claims which will be described later.

The acid generating agent for chemically amplified resist compositions according to embodiments of the present invention is an acid generating agent represented by the following formula (1) or (2):

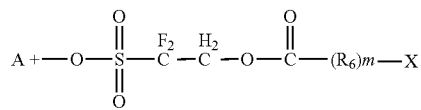

[Formula 1]

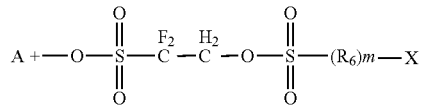

[Formula 2]

wherein in the formula (1) and (2), X represents an unsubstituted or substituted alkyl group having 1 to 20 carbon atoms and selected from alkyl, haloalkyl and alkylsulfonyl, which may have at least one hydrogen atom substituted by an ether group, an ester group, a carbonyl group, an acetal group, a nitrile group, a cyano group, a hydroxyl group, a carboxyl group or an aldehyde group, or represents a perfluoroalkyl group having 1 to 4 carbon atoms; $R_6$ represents an alkyl group having 1 to 10 carbon atoms, an alkoxy group having 1 to 10 carbon atoms, or a heteroatom selected from N, S, F and O; m is an integer from 0 to 2; and A+ is an organic counterion.

In the above formula (1) and formula (2), specific examples of X include —$CH_3$, —$(CH_2)_2CH_3$, —$(CH_2)_4CH_3$, —$(CH_2)_7CH_3$, —$CH(CH_3)CH_3$, —$CH(CH_3)_2CH_3$, —$CH(CH_3)_2$, —$CH_2CH(CH_3)_2$, —$CH_2$—$CH_2(CH_2)_2$—O—$CH_2CH_3$, —$(CH_2)_2$—O—$(CH_2)_2CH_3$, —$CH_2CH(CH_3)_2$ and the like.

X is preferably a divalent or trivalent residue of an alkane having 1 to 30 carbon atoms. In the alkane or cycloalkane, —$CH_2$— may be substituted by —O—, and in the alkane or cycloalkane, one or more hydrogen atoms may be substituted by an alkoxy group having 1 to 6 carbon atoms, a perfluoroalkyl group having 1 to 4 carbon atoms, a hydroxyalkyl group having 1 to 6 carbon atoms, a sulfonyl group having 1 to 6 carbon atoms or a haloalkyl group having 1 to 8 carbon atoms.

As for the acid generating agent of formula (1), preferably one or more species having an anion moiety selected from the following formulas (1-i) to (1-viii), can be used.

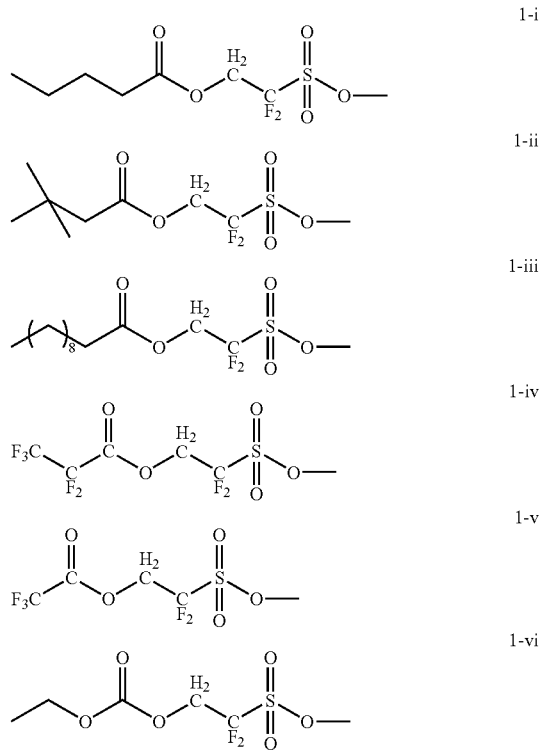

-continued 1-vii
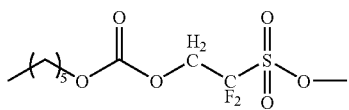

1-viii
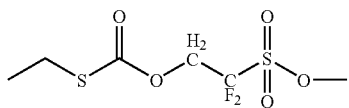

As for the acid generating agent of formula (2), preferably one or more species having an anion moiety selected from the following formulas (2-i) to (2-vi), can be used.

2-i
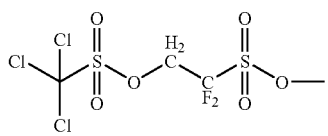

2-ii
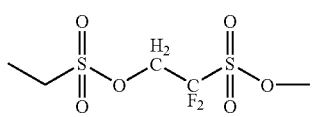

2-iii
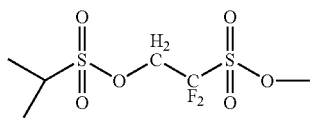

2-iv
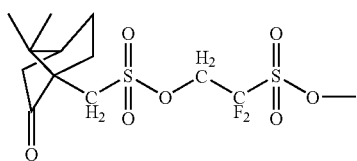

2-v
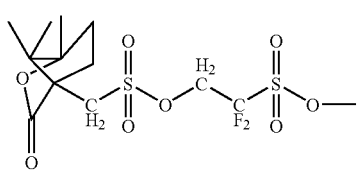

2-vi
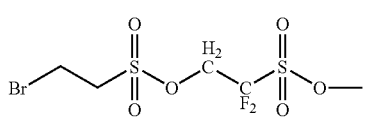

In the formula (1) or formula (2), A+ may comprise a salt having at least one cation selected from the group consisting of cations of the following formulas (3a) and (3b):

[Formula 3a]
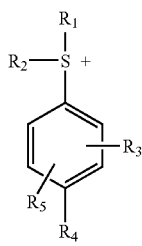

[Formula 3b]
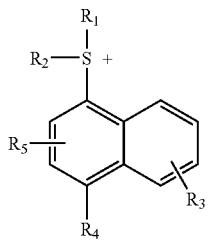

wherein in the formulas (3a) and (3b), $R_1$ and $R_2$ each independently represent an alkyl group, a cycloalkyl group, an allyl group, a perfluoroalkyl group, a benzyl group or an aryl group, each having 1 to 20 carbon atoms; and $R_3$, $R_4$ and $R_5$ each independently represent a hydrogen atom, an alkyl group, a cycloalkyl group, a halogen atom, an alkoxy group, an aryl group, a thiophenoxy group, a thioalkoxy group or an alkoxycarbonylmethoxy group.

In the formula (1) or formula (2), A+ may comprise a salt having at least one cation selected from the group consisting of cations of the following formulas (4a) and (4b):

[Formula 4a]
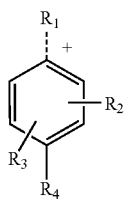

[Formula 4b]
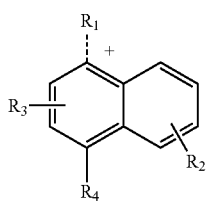

wherein in the formulas (4a) and (4b), $R_1$ and $R_4$ each independently represent an alkyl group, a cycloalkyl group, an allyl group, a perfluoroalkyl group, a benzyl group or an aryl group; and $R_2$ and $R_3$ each independently represent a hydrogen atom, an alkyl group, a cycloalkyl group, a halogen atom, an alkoxy group, an aryl group, a thiophenoxy group, a thioalkoxy group or an alkoxycarbonylmethoxy group.

In the formulas (3a), (3b), (4a) and (4b), examples of the alkyl group include a methyl group, an ethyl group, a propyl group, an isopropyl group, an n-butyl group, a pentyl group, a hexyl group, an octyl group and the like, and examples of the alkoxy group include a methoxy group, an ethoxy group, a propoxy group, a butoxy group, a hexyloxy group, an octyloxy group and the like. Examples of the cyclic hydrocarbon group include a cyclopentyl group, a cyclohexyl group, an adamantyl group, a bicyclohexyl group, a phenyl group, a naphthyl group, a fluorenyl group, a biphenyl group and the like.

The acid generating agent of formula (1) can be produced by a reaction between a salt represented by the following formula (5) and a compound represented by the following formula (9):

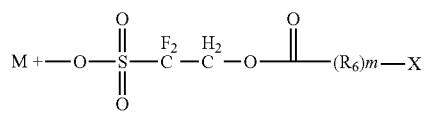

[Formula 5]

wherein X represents an unsubstituted or substituted alkyl group having 1 to 20 carbon atoms and selected from alkyl, haloalkyl and alkylsulfonyl, which may have at least one hydrogen atom substituted by an ether group, an ester group, a carbonyl group, an acetal group, a nitrile group, a cyano group, a hydroxyl group, a carboxyl group or an aldehyde group, or represents a perfluoroalkyl group having 1 to 4 carbon atoms; $R_6$ represents an alkyl group having 1 to 10 carbon atoms, an alkoxy group having 1 to 10 carbon atoms, or a heteroatom selected from N, S, F and O; m is an integer from 0 to 2; and M is lithium (Li), sodium (Na) or potassium (K);

$$A^+ + Z^-$$ [Formula 9]

wherein A+ is an organic counterion; and Z is $OSO_2CF_3$, $OSO_2C_4F_9$, $OSO_2C_8F_{17}$, $N(CF_3)_2$, $N(C_2F_5)_2$, $N(C_4F_9)_2$, $C(CF_3)_3$, $C(C_2F_5)_3$, $C(C_4F_9)_3$, F, Cl, Br, I, $BF_4$, $A_SF_6$ or $PF_6$.

The salt of formula (5) can be produced by a reaction between an alcohol compound represented by the following formula (7) and an acyl compound represented by the following formula (8):

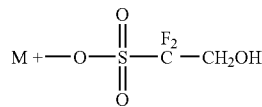

[Formula 7]

wherein M is Li, Na or K;

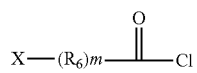

[Formula 8]

wherein X represents an unsubstituted or substituted alkyl group having 1 to 20 carbon atoms and selected from alkyl, haloalkyl and alkylsulfonyl, which may have at least one hydrogen atom substituted by an ether group, an ester group, a carbonyl group, an acetal group, a nitrile group, a cyano group, a hydroxyl group, a carboxyl group or an aldehyde group, or represents a perfluoroalkyl group having 1 to 4 carbon atoms; $R_6$ represents an alkyl group having 1 to 10 carbon atoms, an alkoxy group having 1 to 10 carbon atoms, or a heteroatom selected from N, S, F and O; and m is an integer from 0 to 2.

The alcohol compound of formula (7) can be produced by a reduction reaction of an ester compound represented by the following formula (6):

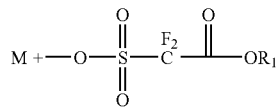

[Formula 6]

wherein $R_1$ is hydrogen, methyl, trifluoromethyl, trichloromethyl, tribromomethyl or triiodomethyl; and M is Li, Na or K.

Meanwhile, the acid generating agent of formula (2) can be produced by a reaction between a salt represented by the following formula (10) and a compound represented by the following formula (9):

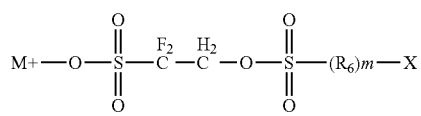

[Formula 10]

wherein X represents an unsubstituted or substituted alkyl group having 1 to 20 carbon atoms and selected from alkyl, haloalkyl and alkylsulfonyl, which may have at least one hydrogen atom substituted by an ether group, an ester group, a carbonyl group, an acetal group, a nitrile group, a cyano group, a hydroxyl-group, a carboxyl group or an aldehyde group, or represents a perfluoroalkyl group having 1 to 4 carbon atoms; $R_6$ represents an alkyl group having 1 to 10 carbon atoms, an alkoxy group having 1 to 10 carbon atoms, or a heteroatom selected from N, S, F and O; m is an integer from 0 to 2; and M is Li, Na or K;

$$A^+ + Z^-$$ [Formula 9]

wherein A+ is an organic counterion; and Z is $OSO_2CF_3$, $OSO_2C_4F_9$, $OSO_2C_8F_{17}$, $N(CF_3)_2$, $N(C_2F_5)_2$, $N(C_4F_9)_2$, $C(CF_3)_3$, $C(C_2F_5)_3$, $C(C_4F_9)_3$, F, Cl, Br, I, $BF_4$, $A_SF_6$ or $PF_6$.

In the formula (1) or formula (2), A+ comprise a salt having at least one cation selected from the group consisting of cations of the following formulas (3a) and (3b), and as for the formula (3a) and formula (3b), preferably one or more species selected from the following formulas (3-i) to (3-xxii) can be used.

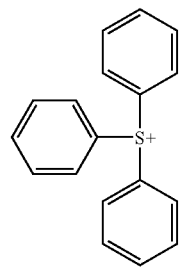

3-i

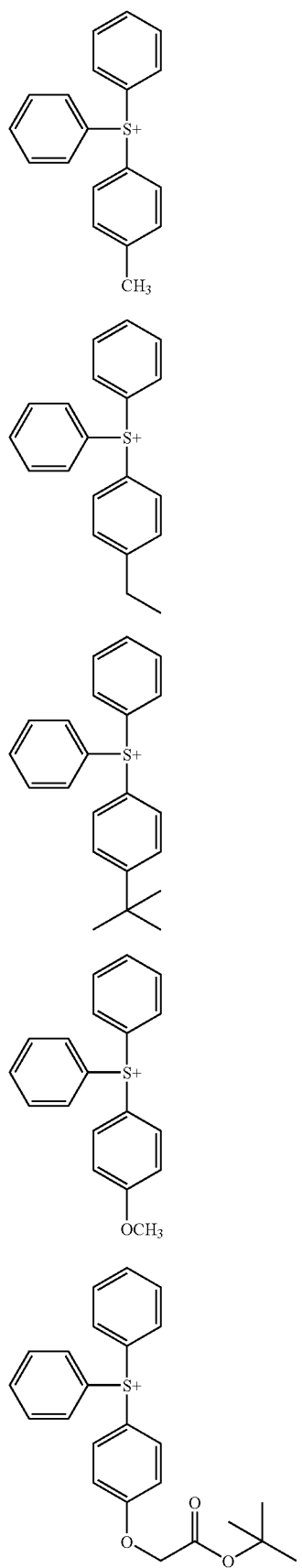
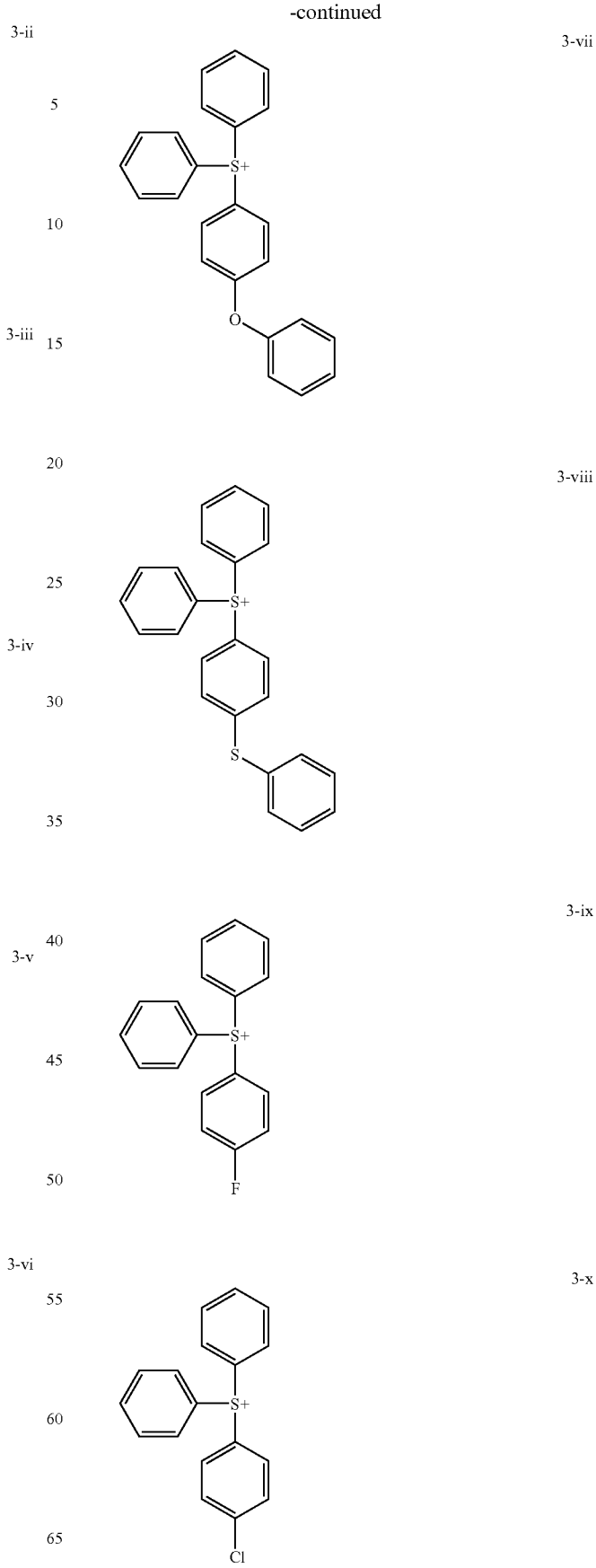

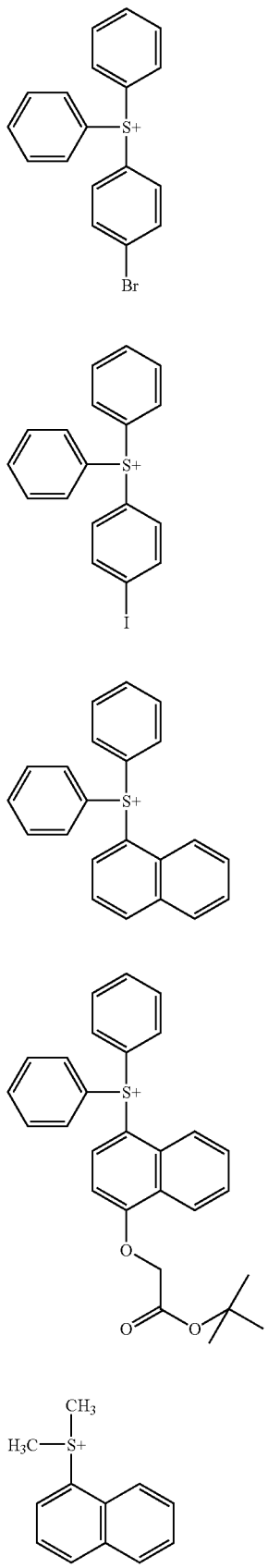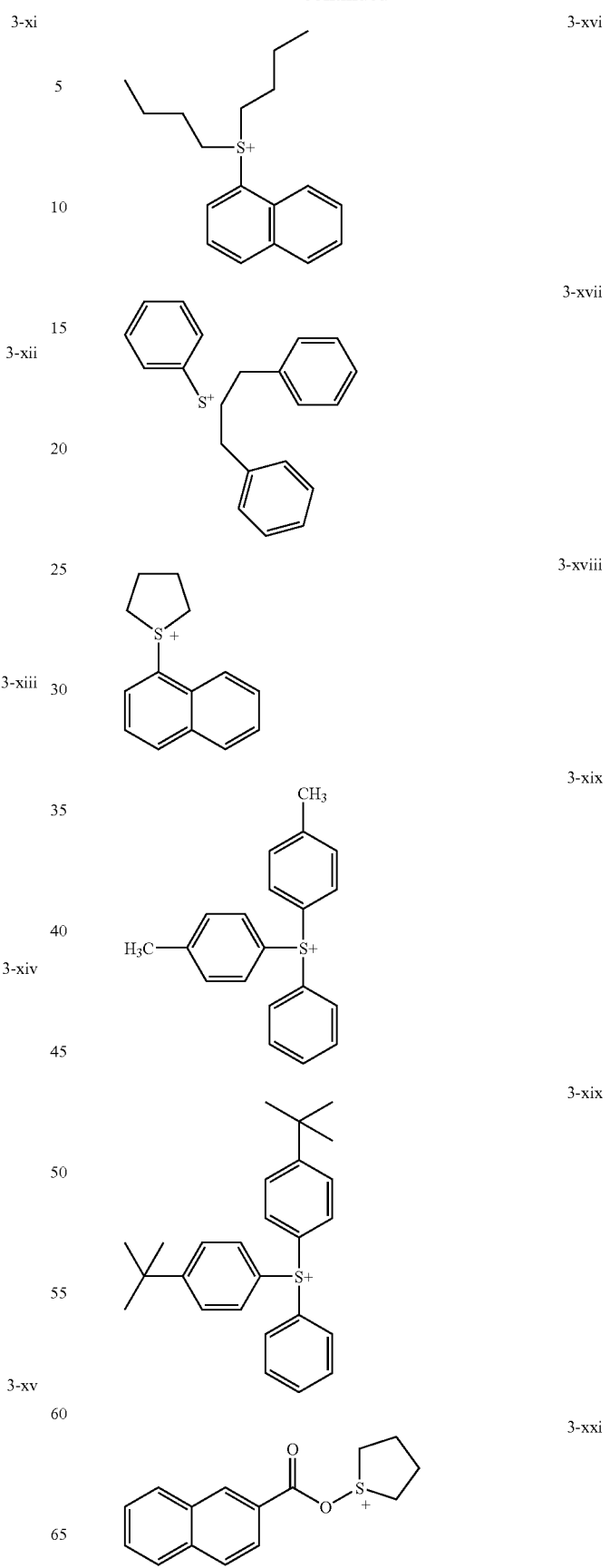

3-xxii

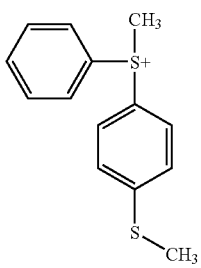

As for the formula (4a) and formula (4b), preferably one or more species selected from the following formulas (4-i) to (4-xiii) can be used.

4-i

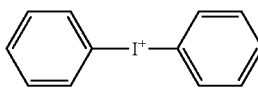

4-ii

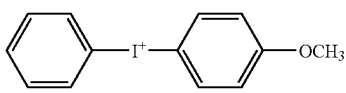

4-iii

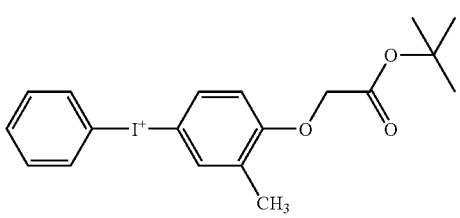

4-iv

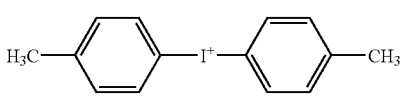

4-v

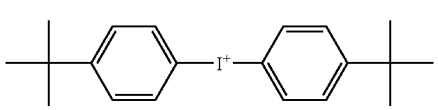

4-vi

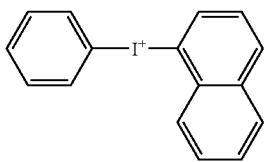

4-vii

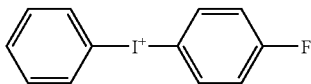

4-viii

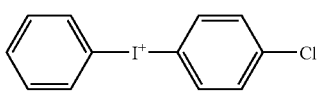

4-viii

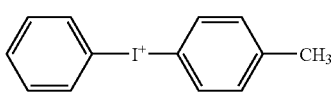

As the method for producing a salt of the formula (1), there may be mentioned a method including mixing dichloromethane, chloroform, dichloroethane or the like with water at a temperature of 0 to 100° C., adding a compound of the formula (5) and a compound of the formula (9) thereto, and allowing the mixture to react.

The amount of use of the compound of formula (5) can be about 1 mole to 2 moles based on 1 mole of the compound of formula (9). If the obtained salt of formula (1) is solid, the salt can be recovered by a solidification method using a mixture of a good solvent and a poor solvent, and if the salt is oily, the salt can be recovered by extraction or concentration.

An example of the method for producing the salt of formula (5) is a method of reacting an alcohol of the formula (7) with acyl chloride of the formula (8).

In such method involving reaction, the alcohol of formula (7) and the acyl chloride of formula (8) are dissolved in a reaction solvent such as dichloromethane, chloroform, dichloroethane, acetonitrile, toluene or the like generally at a temperature of 0 to 100° C., and then a reaction can be induced using a basic catalyst such as triethylamine, diethylamine, pyridine, diethylisopropylamine or the like in an amount of 1 to 2 moles based on 1 mole of the compound of formula (8), and using N,N-dimethylaminopyridine as a catalyst in an amount of 0.1 to 0.5 moles based on 1 mole of the mixture.

In the method for producing the alcohol of formula (7), an ester compound such as that represented by formula (6) is dissolved in a solvent mixture of tetrahydrofuran and an alcohol such as methanol, ethanol or propanol, and sodium borohydride ($NaBH_4$) is slowly added dropwise to the solution in an ice bath.

When the dropwise addition is completed, the mixture is stirred in an oil bath at 60° C. for about 4 hours, and then the reaction mixture is quenched with distilled water to remove the solvent. The reaction mixture from which the solvent has been removed is dissolved again in distilled water, and then is acidified using concentration hydrochloric acid to obtain a pH value of 5 to 6.

The mixture is concentrated again, and then methanol is added to make a slurry, which is then filtered. The filtrate is washed using hexane, and then concentrated again. The resultant is subjected to crystallization using diethyl ether, and then filtered and dried to obtain an alcohol such as that represented by the formula (7).

The chemically amplified resist composition containing the acid generating agent of the present invention can contain the acid generating agent in an amount of 1 to 20 parts by weight based on 100 parts by weight of polymer, and the type of the polymer is not limited.

If the amount is less than 1 part by weight, an appropriate pattern as a result of chemical amplification cannot be obtained, and if the amount exceeds 20 parts by weight, excessive generation of acid causes severe pattern loss, and thus a desired pattern cannot be obtained.

Hereinafter, Examples and Comparative Examples of the invention will be described. However, the following Examples are merely preferred examples of the invention, and the present invention is not intended to be limited by the following Examples.

SYNTHESIS EXAMPLE 1

Production of diphenylmethylphenyl-(3,3-dimethylbutyric acid-2,2-difluoro-2-sulfoethyl Ester) Sulfonium Salt <1> Synthesis of 1,1-difluoro-2-hydroxyethanesulfonic Acid Sodium Salt In an ice bath, 83 g of difluorosulfoacetic acid ethyl ester sodium salt was dissolved in 160 ml of methanol and 1.2 L of THF, and 44 g of sodium borohydride (NaBH$_4$) was slowly added dropwise. After completing the dropwise addition, the ice bath was removed, and the temperature of the mixture was elevated to 60° C., at which temperature the mixture was stirred for about 4 hours.

After the reaction, the reaction mixture was quenched with distilled water, and then the solvent was removed. The crude reaction mixture was dissolved in dissolved water, and the resultant was acidified with concentrated hydrochloric acid to obtain a pH value of 5 to 6. After concentrating the mixture, methanol was added, and the slurry was filtered to remove inorganic salts. The filtrate was washed two times with hexane, the methanol layer was concentrated again, and the resultant was subjected to crystallization from diethyl ether. The white solid obtained after filtration was dried in vacuum, and the structure was confirmed by $^1$H-NMR. The obtained spectrum is shown in FIG. 1. After the filtration and drying, 68.5 g (yield 95%) of 1,1-difluoro-2-hydroxyethanesulfonic acid sodium salt was obtained.

$^1$H-NMR (D$_2$O): –(ppm) 4.18 (t, 2H)

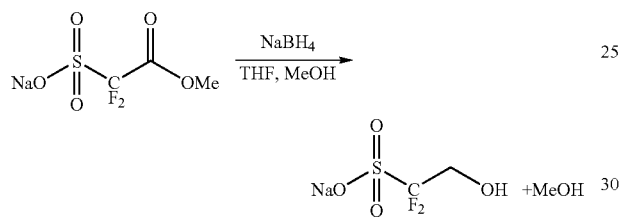

<2> Synthesis of 3,3-dimethylbutyric acid-2,2-difluoro-2-sulfoethyl Ester Sodium Salt In an ice bath, 10 g of 1,1-difluoro-2-hydroxyethanesulfonic acid sodium salt produced above and 7.31 g of t-butylacetyl chloride were dissolved in 150 ml of dichloroethane, and stirred at 0° C. 7.57 ml of triethylamine was slowly added dropwise at 0° C., and then 0.5 g of DMAP was added thereto. The reaction temperature was elevated to ambient temperature, and the mixture was stirred for 2 hours.

After completion of the reaction, the reaction mixture was washed twice with 30 ml of distilled water, and then the solvent was removed. The resultant was made into a slurry with ethyl ether, and then filtered. After the filtration, the filter cake was washed using distilled water and ethyl ether, and then dried in vacuum. The structure of the product was confirmed by $^1$H-NMR, and thus 9.92 g (64.8%) of 3,3-dimethylbutyric acid 2,2-difluoro-2-sulfoethyl ester sodium salt represented by the following structural formula was obtained.

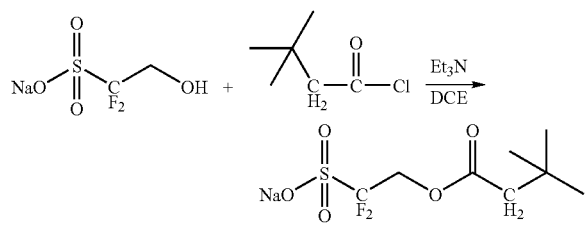

<3> 7 g of 3,3-dimethylbutyric acid-2,2-difluoro-2-sulfoethyl ester sodium salt produced in <2> and 9.6 g of diphenylmethylphenylsulfonium trifluoromethanesulfonate salt were dissolved in 100 ml of dichloromethane and 100 ml of water, and a bilayer reaction was performed with vigorous stirring for 3 hours.

After the stirring, the organic layer was sampled to confirm the progress of the reaction by $^{19}$F-NMR. When the reaction was completed, the organic layers were combined, the solvent was removed, and the residue was washed using dichloromethane, which is a good solvent, and hexane, which is a poor solvent. The solvent was removed, and the residue was dried under reduced pressure, to obtain 12.02 g (yield 99.5%) of diphenylmethylphenyl-(3,3-dimethylbutyric acid 2,2-difluoro-2-sulfoethyl-ester)sulfonium salt. The structure was confirmed by $^1$H-NMR.

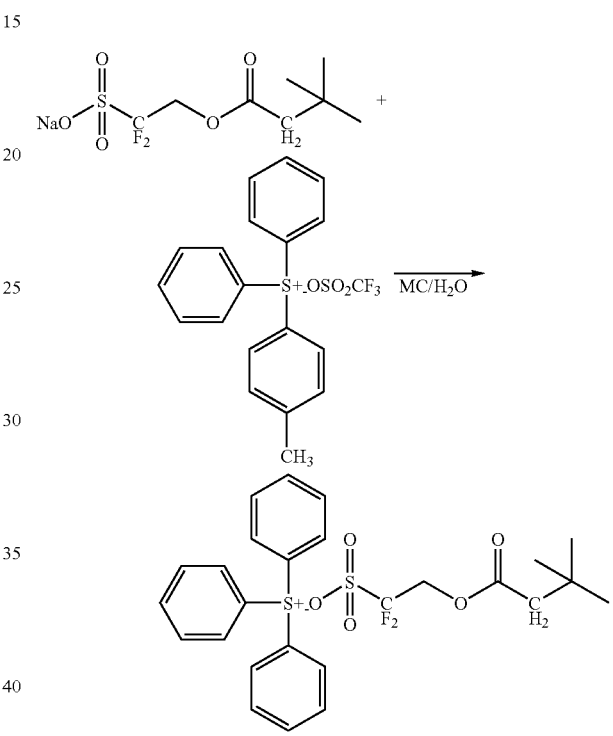

SYNTHESIS EXAMPLE 2

Production of diphenylmethylphenyl-(heptanoic acid 2,2-difluoro-2-sulfoethyl ester) Sodium Salt <1> Production of heptanoic acid 2,2-difluoro-2-sulfoethyl ester Sodium Salt 10 g of hydroxymethyldifluoromethanesulfonate sodium salt produced in <1> of [Synthesis Example 1] and 8.07 g of heptanoyl chloride were dissolved in 150 ml of dichloroethane, and the mixture was stirred at ambient temperature. 11.36 ml of triethylamine was slowly added dropwise at 0° C., and then 0.5 g of DMAP was added. The reaction temperature was elevated to ambient temperature, and the mixture was stirred for 2 hours.

After completion of the reaction, the reaction mixture was extracted with methyl chloride (MC), and then the solvent was removed. The residue was made into a slurry with ethyl ether, and was filtered. After the filtration, the filter cake was washed using distilled water and ethyl ether, and was dried in vacuum. The structure of the product was confirmed by 1H-NMR, and thus 6.84 g (yield 46.3%) of heptanoic acid 2,2-difluoro-2-sulfoethyl ester sodium salt having the following structural formula was obtained.

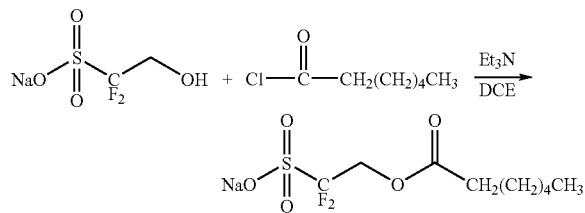

<2> Production of diphenylmethylphenyl (heptanoic acid 2,2-difluoro-2-sulfoethyl Ester) Sodium Salt 3 g of heptanoic acid 2,2-difluoro-2-sulfoethyl ester sodium salt produced in <1> and 3.32 g of diphenylmethylphenylsulfonium trifluoromethanesulfonate salt were dissolved in 30 ml of dichloromethane and 30 ml of water, and a bilayer reaction was performed with vigorous stirring for 3 hours.

After the stirring, the organic layer was sampled to confirm the progress of the reaction by $^{19}$F-NMR. When the reaction was completed, the organic layers were combined, the solvent was removed, and the residue was washed using dichloromethane, which is a good solvent, and hexane, which is a poor solvent. The solvent was removed, and the residue was dried under reduced pressure, to obtain 4.59 g (yield 84.7%) of diphenylmethylphenyl-(heptanoic acid 2,2-difluoro-2-sulfoethyl-ester)sulfonium salt. The structure was confirmed by $^1$H-NMR.

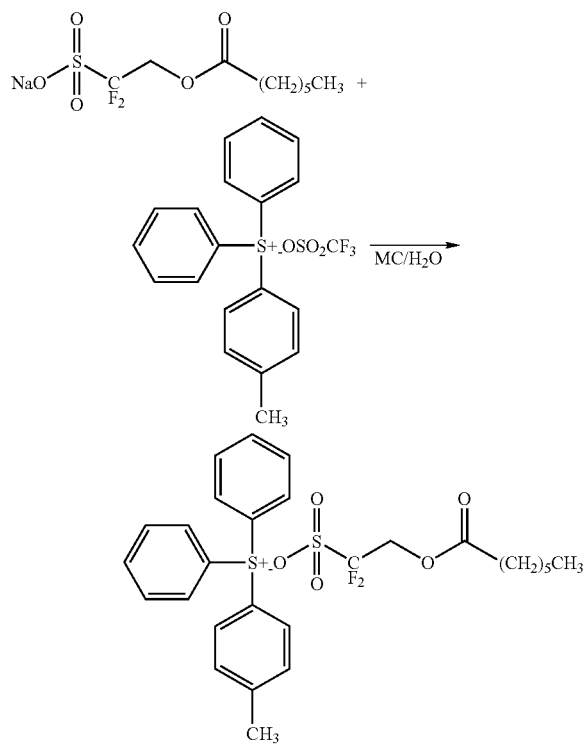

SYNTHESIS EXAMPLE 3

Diphenylmethylphenyl-(2-ethoxycarbonyl-1,1-difluoroethanesulfonic Acid) Sodium Salt <1> Production of 2-ethoxycarbonyl-1,1-difluoroethanesulfonic Acid Sodium Salt 8 g (yield 57.6%) of 2-ethoxycarbonyl-1,1-difluoroethanesulfonic acid sodium salt was obtained in the same manner as in <2> of [Synthesis Example 1], except that 5.89 g of ethyl chloroformate was used instead of t-butylacetyl chloride as the reactant with alcohol. The structure of the product was confirmed by $^1$H-NMR.

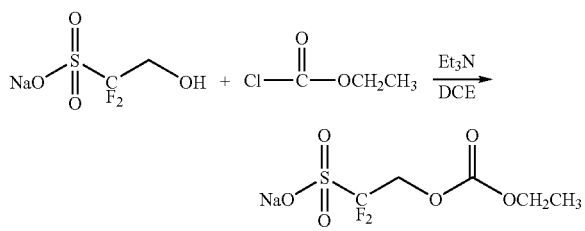

<2> Diphenylmethylphenyl-(2-ethoxycarbonyl-1,1-difluoroethanesulfonic Acid) Sodium Salt 9.1 g (yield 95%) of diphenylmethylphenyl-(2-ethoxycarbonyl-1,1-difluoroethanesulfonic acid) sodium salt as shown below was obtained in the same manner as in <3> of [Synthesis Example 1], except that 8 g of the 2-ethoxycarbonyl-1,1-difluoroethanesulfonic acid sodium salt produced in <1> above was used instead of t-butylacetyloxymethyldifluorosulfonate sodium salt in the reaction with the diphenylmethylphenylsulfonium trifluoromethanesulfonate salt. The structure of the product was confirmed by $^1$H-NMR.

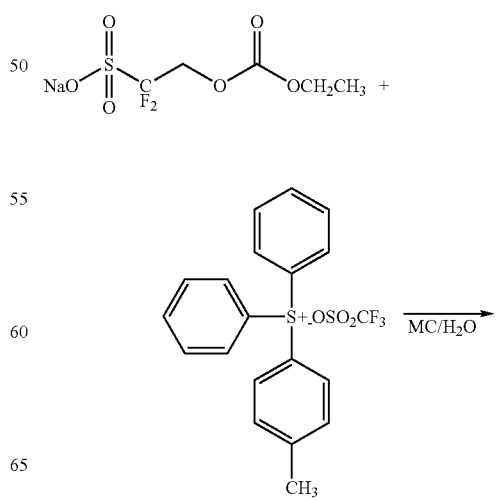

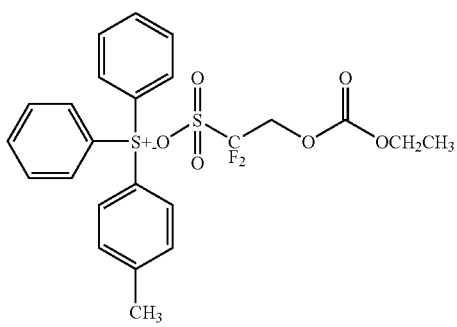

SYNTHESIS EXAMPLE 4

Production of diphenylmethylphenyl-(isobutyric acid 2,2-difluoro-2-sulfoethyl Ester) Sodium Salt <1> Production of isobutyric acid 2,2-difluoro-2-sulfoethyl Ester Sodium Salt 7.5 g (yield 82%) of isobutyric acid 2,2-difluoro-2-sulfoethyl ester sodium salt as shown below was obtained in the same manner as in <2> of [Synthesis Example 1], except that 6.95 g of isobutyryl chloride was used instead of t-butylacetyl chloride as the reactant to react with the alcohol. The structure of the product was confirmed by $^1$H-NMR.

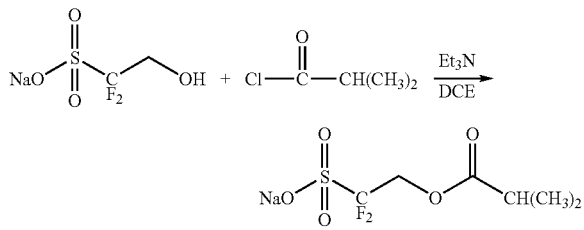

<2> Diphenylmethylphenyl-(isobutyric acid 2,2-difluoro-2-sulfoethyl Ester) Sodium Salt 5.62 g (98%) of diphenylmethylphenyl(isobutyric acid 2,2-difluoro-2-sulfoethyl ester) sodium salt as shown below was obtained in the same manner as in <3> of [Synthesis Example 1], except that 4 g of the isobutyric acid 2,2-difluoro-2-sulfoethyl ester sodium salt produced in <1> of Synthesis Example 4 was used instead of t-butylacetyloxymethylifluorosulfonate sodium salt in the reaction with the diphenylmethylphenylsulfonium trifluoromethanesulfonate salt. The structure of the product was confirmed by $^1$H-NMR.

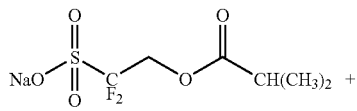

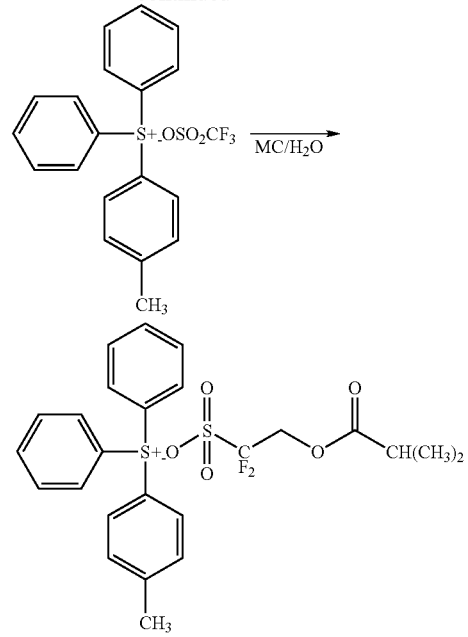

SYNTHESIS EXAMPLE 5

5.72 g of the 3,3-dimethylbutyric acid 2,2-difluoro-2-sulfoethyl ester sodium salt produced in <2> of Synthesis Example 1, and 10 g of diphenyl-t-butoxycarbonylmethoxyphenylsulfonium trifluoromethanesulfonate salt were dissolved in 100 ml of dichloromethane and 100 ml of water, and a bilayer reaction was performed with vigorous stirring for 3 hours.

After the stirring, the organic layer was sampled to confirm the progress of the reaction by $^{19}$F-NMR. When the reaction was completed, the organic layers were combined, the solvent was removed, and the residue was washed using dichloromethane, which is a good solvent, and hexane, which is a poor solvent. The solvent was removed, and the residue was dried under reduced pressure, to obtain 11.4 g (yield 94.8%) of diphenyl-t-butoxycarbonylmethoxyphenyl-3,3-dimethylbutyric acid 2,2-difluoro-2-sulfoethyl ester sodium salt. The structure was confirmed by $^1$H-NMR.

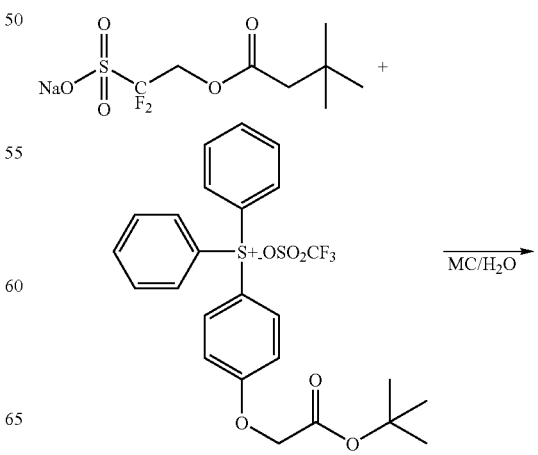

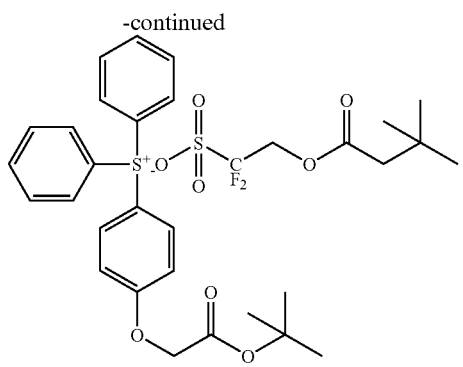

SYNTHESIS EXAMPLE 6

7.22 g of the 3,3-dimethylbutyric acid 2,2-difluoro-2-sulfoethyl ester sodium salt produced in <2> of Synthesis Example 1, and 10 g of diphenylfluorophenylsulfonium trifluoromethanesulfonate salt were dissolved in 100 ml of dichloromethane and 100 ml of water, and a bilayer reaction was performed with vigorous stirring for 3 hours.

After the stirring, the organic layer was sampled to confirm the progress of the reaction by $^{19}$F-NMR. When the reaction was completed, the organic layers were combined, the solvent was removed, and the residue was washed using dichloromethane, which is a good solvent, and hexane, which is a poor solvent. The solvent was removed, and the residue was dried under reduced pressure, to obtain 13.1 g (yield 94.8%) of diphenylfluorophenyl-3,3-dimethylbutyric acid 2,2-difluoro-2-sulfoethyl ester sodium salt. The structure was confirmed by $^1$H-NMR.

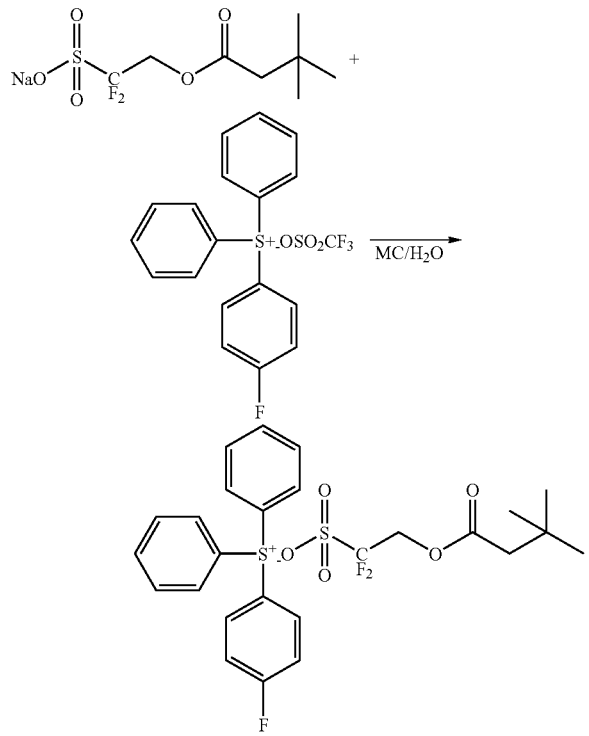

RESIN SYNTHESIS EXAMPLE 1

3-Bicyclo[2.2.1]hept-5-en-2-yl-3-hydroxypropionic acid t-butyl ester (hereinafter, abbreviated to BHP), 1-methyladamantane acrylate and γ-butyrolactone methylacrylate were added in a molar ratio of 1:1:1 (33 parts by weight:33 parts by weight:33 parts by weight), and a reaction was allowed to proceed at 65° C. for 16 hours using 1,4-dioxane as a polymerization solvent in an amount of three-fold the total mass of the reaction monomers, and using azobisisobutyronitrile as an initiator in a proportion of 4% by mole based on the total molar amount of the monomers.

After the reaction, the reaction solution was subjected to precipitation with n-hexane, and the resulting precipitate was dried in vacuum to obtain a resin as shown below. As a result, a copolymer having a weight average molecular weight of about 8,500 was obtained.

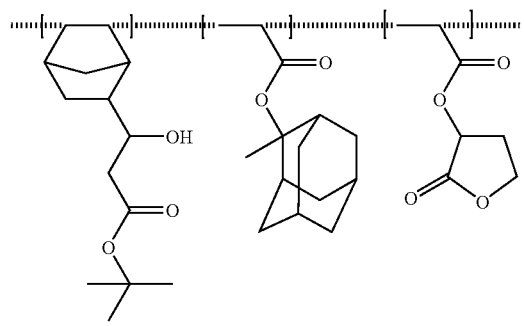

PREPARATION OF RESIST, EXAMPLES 1 TO 3 AND COMPARATIVE EXAMPLE 1

Example 1

Preparation of Resist 100 parts by weight of the resin obtained in Resin Synthesis Example 1, 4 parts by weight of the diphenylmethylphenyl-(3,3-dimethylbutyric acid 2,2-difluoro-2-sulfoethyl ester) sulfonium salt prepared in Synthesis Example 1 as an acid generating agent, and 0.5 parts by weight of tetramethylammonium hydroxide as a basic additive were dissolved in 1000 parts by weight of propylene glycol methyl ether acetate, and then the solution was filtered through a membrane filter having a pore size of 0.2 μm. Thus, a resist was prepared.

The obtained resist solution was coated on a substrate using a spinner, and dried at 110° C. for 90 seconds to form a film having a thickness of 0.20 μm. The formed film was exposed using an ArF excimer laser stepper (lens aperture: 0.78), and then was subjected to heat treatment at 110° C. for 90 seconds. Subsequently, the film was developed with a 2.38 wt % aqueous solution of tetramethylammonium hydroxide for 40 seconds, washed and dried to form a resist pattern.

The developability using an aqueous solution of tetramethylammonium hydroxide, and the adhesiveness of the formed resist pattern to a substrate were good, and the resolution was 0.08 μm, while the sensitivity was 13 mJ/cm$^2$.

From the results of Examples, in the case of line edge roughness (LER), the pattern roughness was observed for 0.10-μm line-and-space (L/S) patterns formed after development, and the improvement in terms of LER was scored from 1 to 5, as compared with the pattern obtained in Comparative Example which was graded as 1 (a larger number corresponds to better LER).

In the case, of sensitivity, the amount of exposure to form a 0.10-μm line-and-space (L/S) pattern at a line width of 1:1 was taken as the optimum amount of exposure, and this optimum amount of exposure was taken as sensitivity. The minimum pattern dimension obtained with the optimum amount of exposure was taken as resolution.

Examples 1 to 3

PAG obtained in Synthesis Example 1, 2 or 3, the resin produced in Resin Synthesis Example 1, and a basic additive were dissolved in 1000 parts by weight of propylene glycol methyl ether acetate, and then the solution was filtered through a membrane filter having a pore size of 0.2 μm, to prepare a resist composition as indicated in Table 1 (provided that the unit is parts by weight). The resist composition was used to form a positive type resist pattern in the same manner as in Example 1, and then various evaluations were performed therewith. The results of evaluation are presented in Table 1.

TABLE 1

| | Resin (100 parts by weight) | *PAG (parts by weight) | *Base (parts by weight) | Sensitivity (mJ/cm$^2$) | Resolution (nm) | LER |
|---|---|---|---|---|---|---|
| Example 1 | Resin Synthesis Example 1 | 4.0 | 0.5 | 13 | 80 | 4 |
| Example 2 | Resin Synthesis Example 1 | 4.0 | 0.5 | 12 | 80 | 3 |
| Example 3 | Resin Synthesis Example 1 | 4.0 | 0.5 | 12 | 70 | 3 |
| Comparative Example 1 | Resin Synthesis Example 1 | 4.0 | 0.5 | 14 | 90 | 1 |

*Type of PAG used in Table 1
Example 1: Diphenylmethylphenyl-(3,3-dimethylbutyric acid 2,2-difluoro-2-sulfoethyl ester) sulfonium salt of Synthesis Example 1
Example 2: Diphenylmethylphenyl-(heptanoic acid 2,2-difluoro-2-sulfoethyl ester) sodium salt of Synthesis Example 2
Example 3: Diphenylmethylphenyl-(2-ethoxycarbonyl-1, 1-difluoroethanesulfonic acid) sodium salt of Synthesis Example 3
Comparative Example 1: Triphenylsulfonium triflate

What is claimed is:

1. An acid generating agent represented by the following formula (1):

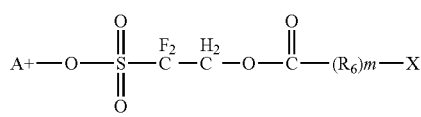

[Formula 1]

wherein X represents an unsubstituted or substituted non-cyclic alkyl group having 1 to 20 carbon atoms and selected from alkyl, haloalkyl and alkylsulfonyl, which may have at least one hydrogen atom substituted by an ether group, an ester group, a carbonyl group, an acetal group, a nitrile group, a cyano group, a hydroxyl group, a carboxyl group or an aldehyde group, or represents a perfluoroalkyl group having 1 to 4 carbon atoms; $R_6$ represents an alkyl group having 1 to 10 carbon atoms, an alkoxy group having 1 to 10 carbon atoms, or a heteroatom selected from nitrogen (N), sulfur (S), fluo-rine (F) and oxygen (O); m is an integer from 0 to 2; and A+ is an organic counterion.

2. The acid generating agent according to claim 1, wherein A+ is at least one cation selected from the group consisting of cations represented by the following formulas 3a and 3b:

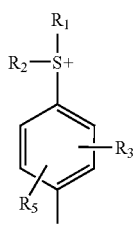

[Formula 3a]

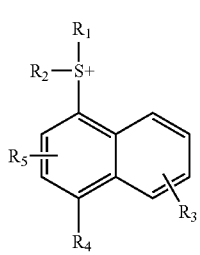

[Formula 3b]

wherein in the formulas 3a and 3b, $R_1$ and $R_2$ each independently represent an alkyl group, a cycloalkyl group, an allyl group, a perfluoroalkyl group, a benzyl group or an aryl group, each having 1 to 20 carbon atoms; and $R_3$, $R_4$ and $R_5$ each independently represent a hydrogen atom, an alkyl group, a cycloalkyl group, a halogen atom, an alkoxy group, an aryl group, a thiophenoxy group, a thioalkoxy group or an alkoxycarbonylmethoxy group.

3. The acid generating agent according to claim 1, wherein A+ is at least one cation selected from the group consisting of cations represented by the following formulas 4a and 4b:

[Formula 4a]

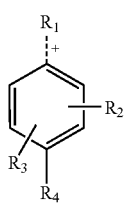

[Formula 4b]

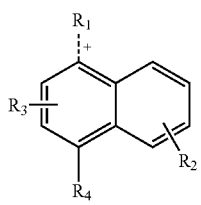

wherein in the formulas (4a) and (4b), $R_1$ and $R_4$ each independently represent an alkyl group, a cycloalkyl group, an allyl group, a perfluoroalkyl group, a benzyl group or an aryl group; and $R_2$ and $R_3$ each independently represent a hydrogen atom, an alkyl group, a cycloalkyl group, a halogen atom, an alkoxy group, an aryl group, a thiophenoxy group, a thioalkoxy group or an alkoxycarbonylmethoxy group.

4. The acid generating agent according to claim 1, wherein the anion moiety of the acid generating agent is at least one selected from groups represented by the following formulas (1-i) to (1-viii)

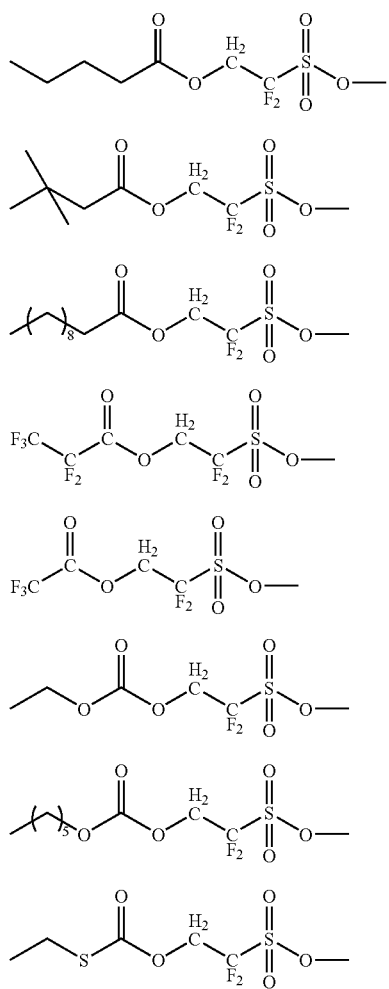

5. The acid generating agent according to claim 1, wherein the acid generating agent is produced by a reaction between a salt represented by the following formula (5) and a compound represented by the following formula (9):

[Formula 5]

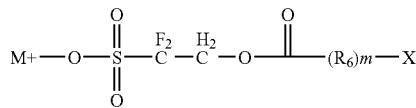

wherein X represents an unsubstituted or substituted non-cyclic alkyl group having 1 to 20 carbon atoms and selected from alkyl, haloalkyl and alkylsulfonyl, which may have at least one hydrogen atom substituted by an ether group, an ester group, a carbonyl group, an acetal group, a nitrile group, a cyano group, a hydroxyl group, a carboxyl group or an aldehyde group, or represents a perfluoroalkyl group having 1 to 4 carbon atoms; $R_6$ represents an alkyl group having 1 to 10 carbon atoms, an alkoxy group having 1 to 10 carbon atoms, or a heteroatom selected from N, S, F and O; m is an integer from 0 to 2; and M is lithium (Li), sodium (Na) or potassium (K);

$$A^+ + Z^-$$ [Formula 9]

wherein A+ is an organic counterion; and Z is $OSO_2CF_3$, $OSO_2C_4F_9$, $OSO_2C_8F_{17}$, $N(CF_3)_2$, $N(C_2F_5)_2$, $N(C_4F_9)_2$, $C(CF_3)_3$, $C(C_2F_5)_3$, $C(C_4F_9)_3$, F, Cl, Br, I, $BF_4$, $A_sF_6$ or $PF_6$.

6. The acid generating agent according to claim 5, wherein the salt of formula (5) is produced by a reaction between an alcohol compound represented by the following formula (7) and an acyl compound represented by the following formula (8):

[Formula 7]

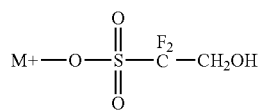

wherein M is Li, Na or K;

[Formula 8]

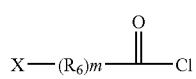

wherein X represents an unsubstituted or substituted non-cyclic alkyl group having 1 to 20 carbon atoms and selected from alkyl, haloalkyl and alkylsulfonyl, which may have at least one hydrogen atom substituted by an ether group, an ester group, a carbonyl group, an acetal group, a nitrile group, a cyano group, a hydroxyl group, a carboxyl group or an aldehyde group, or represents a perfluoroalkyl group having 1 to 4 carbon atoms; $R_6$ represents an alkyl group having 1 to 10 carbon atoms, an alkoxy group having 1 to 10 carbon atoms, or a heteroatom selected from N, S, F and O; and m is an integer from 0 to 2.

7. The acid generating agent according to claim 6, wherein the alcohol compound of formula (7) is produced by a reduction reaction of an ester compound represented by the following formula (6):

[Formula 6]

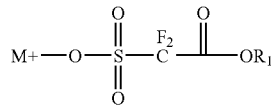

wherein $R_1$ is hydrogen, methyl, trifluoromethyl, trichloromethyl, tribromomethyl or triiodomethyl; and M is Li, Na or K.

8. A chemically amplified resist composition comprising the acid generating agent of claim 1 and a copolymer.

9. The chemically amplified resist composition according to claim 8, wherein the acid generating agent is contained in an amount of 1 to 20 parts by weight based on 100 parts by weight of the copolymer.

* * * * *